(12) United States Patent
Taghipour

(10) Patent No.: US 7,442,312 B2
(45) Date of Patent: Oct. 28, 2008

(54) ENERGY-BASED PROCESS FOR FLUID TREATMENT AND SYSTEM THEREOF

(75) Inventor: Fariborz Taghipour, Vancouver (CA)

(73) Assignee: Trojan Technologies Inc. (CA)

( * ) Notice: Subject to any disclaimer, the term of this patent is extended or adjusted under 35 U.S.C. 154(b) by 93 days.

(21) Appl. No.: 10/486,967

(22) PCT Filed: Aug. 19, 2002

(86) PCT No.: PCT/CA02/01282

§ 371 (c)(1),
(2), (4) Date: Aug. 23, 2004

(87) PCT Pub. No.: WO03/016222

PCT Pub. Date: Feb. 27, 2003

(65) Prior Publication Data

US 2004/0262235 A1  Dec. 30, 2004

Related U.S. Application Data

(60) Provisional application No. 60/312,792, filed on Aug. 17, 2001.

(51) Int. Cl.
*C02F 1/32* (2006.01)
(52) U.S. Cl. .................................... 210/748
(58) Field of Classification Search ................ 210/748
See application file for complete search history.

(56) References Cited

U.S. PATENT DOCUMENTS

| | | | |
|---|---|---|---|
| 3,511,776 A | 5/1970 | Avampato | |
| 3,603,788 A | 9/1971 | Miraidi, et al. | |
| 3,904,882 A | 9/1975 | Lund, et al. | |
| 4,317,041 A * | 2/1982 | Schenck | 250/435 |
| 5,512,253 A | 4/1996 | Woodbridge et al. | |

FOREIGN PATENT DOCUMENTS

DE  198 14 112  10/1998
DE  197 48 098  7/1999

OTHER PUBLICATIONS

Kielburger G: Elektronenstrahltechnik zur Aufbereitjung schadstoffhaltiger Wasser und Schlamme, WLB Wasser, Luft Und Boden, No. 11-12, 1994, pp. 24-26, XP002222064 the whole document.

* cited by examiner

*Primary Examiner*—Robert A Hopkins
(74) *Attorney, Agent, or Firm*—Katten Muchin Rosenman LLP

(57) ABSTRACT

A process for treating a fluid which comprises the step of exposing the fluid to ultraviolet radiation and high-energy ionizing radiation. It has been discovered that combining ultraviolet radiation with high-energy ionizing radiation in the treatment of a fluid results in synergistic performances of the treatment process—e.g., improvement in the inactivation or killing of microorganisms in the fluid, in destruction of organic contaminants and the like. More specifically, fluid treatment performance is improved to a level typically not possible when using ultraviolet radiation and high-energy ionizing radiation separately.

32 Claims, 2 Drawing Sheets

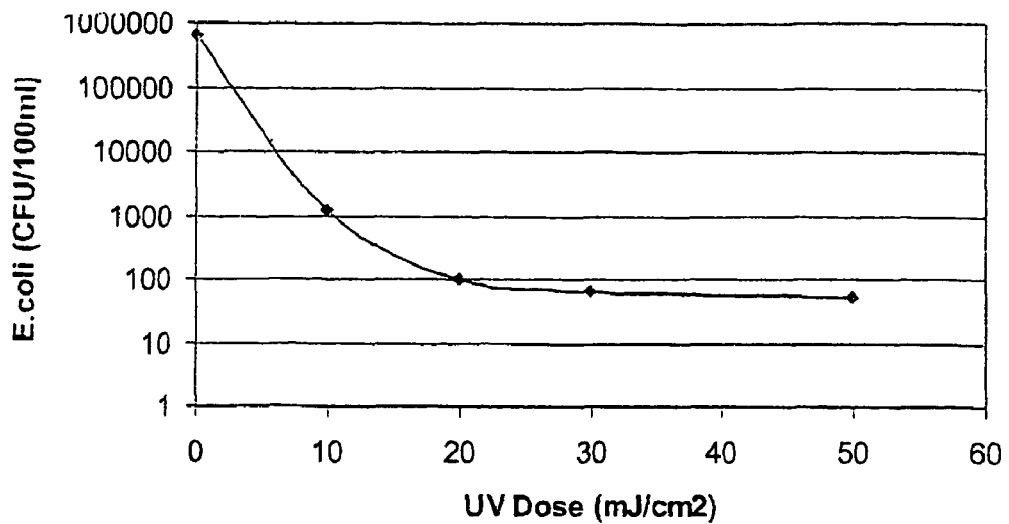
Figure 1. *E.coli* inactivation in primary wastewater effluent by UV irradiation
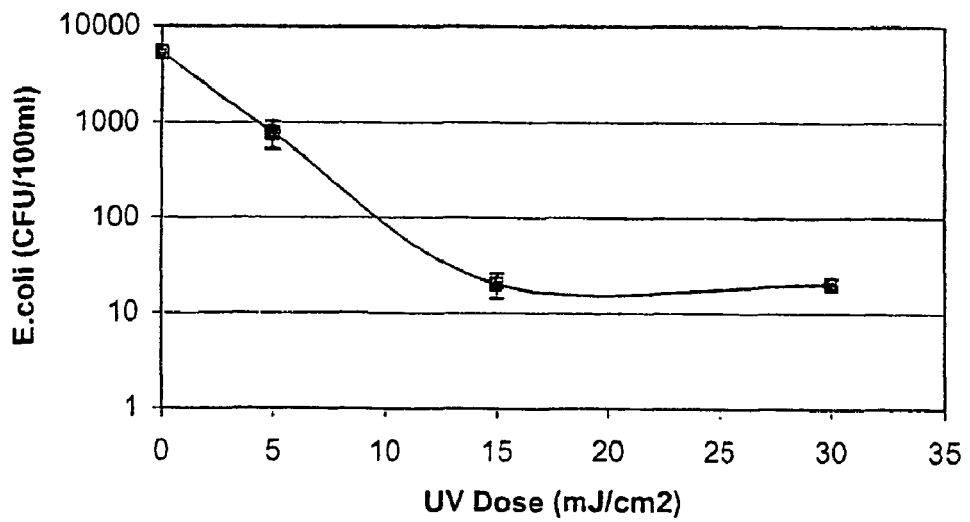
Figure 2. *E.coli* inactivation in secondary wastewater effluent by UV irradiation

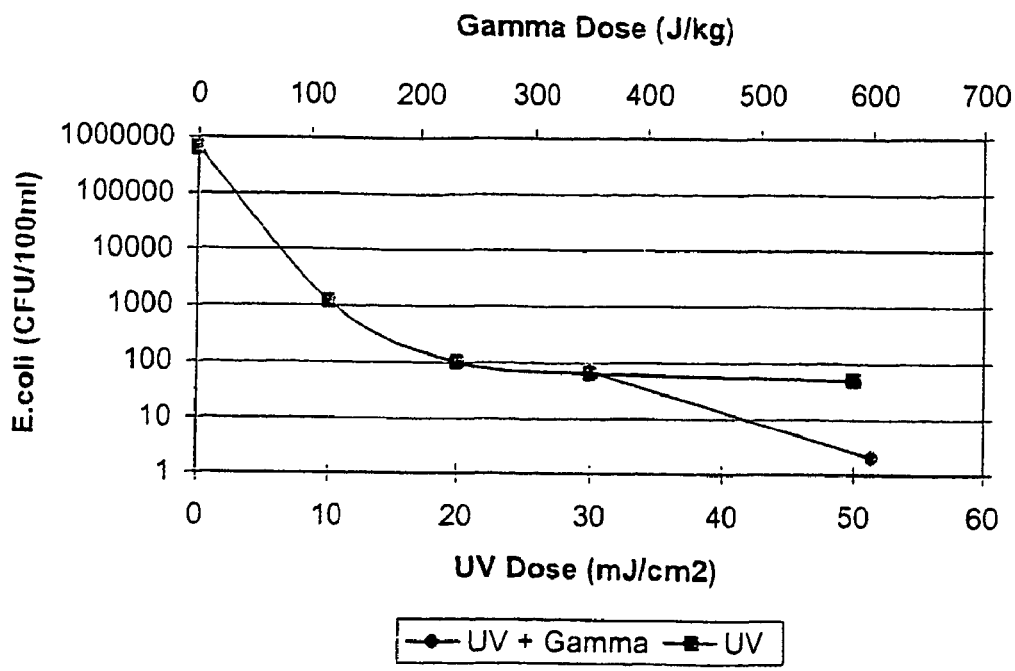
Figure 3. *E.coli* inactivation in primary wastewater effluent by UV irradiation followed by gamma irradiation
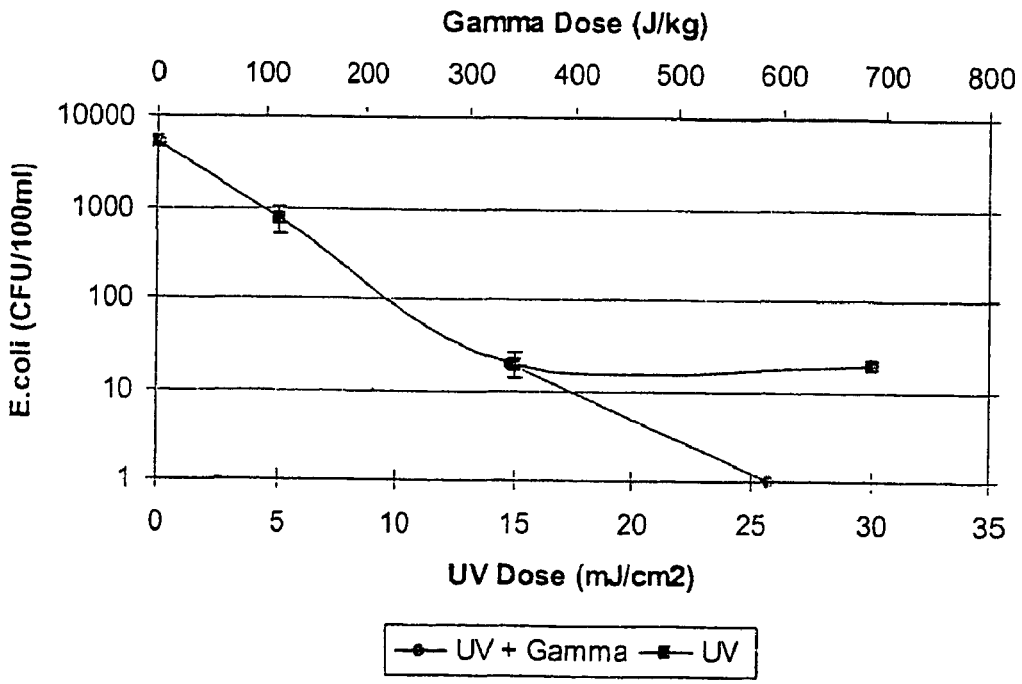
Figure 4. *E.coli* inactivation in secondary wastewater effluent by UV irradiation followed by gamma irradiation

ENERGY-BASED PROCESS FOR FLUID TREATMENT AND SYSTEM THEREOF This application is a 371 of PCT/CA02/01282, filed Aug. 19, 2002 (designating the U.S.; and which published in English in WO 03/016222 on Feb. 27, 2003), which claims the benefit of U.S. Provisional Patent Application No. 60/312,792, Aug. 17, 2001, incorporated herein by reference.

TECHNICAL FIELD

In one of its aspects, the present invention relates to an energy-based process for treatment of a fluid. In another of its aspects, the present invention relates to system for carrying out energy-based treatment of a fluid.

BACKGROUND ART

Various forms of energy-based treatment of a fluid are known.

Indeed, the assignee of the present invention is the assignee of a number United States patents relating to ultraviolet (UV) radiation treatment of fluids such as municipal wastewater, municipal drinking water, industrial waste water, industrial process water, domestic drinking water and the like. See, for example, one or more of the following patents:

U.S. Pat. No. 4,482,809;
U.S. Pat. No. 4,872,980;
U.S. Pat. No. 5,006,244;
U.S. Pat. No. 5,418,370;
U.S. Pat. No. 5,471,063;
U.S. Pat. No. 5,504,335;
U.S. Pat. No. 5,514,871;
U.S. Pat. No. 5,539,209;
U.S. Pat. No. 5,539,210;
U.S. Pat. No. 5,580,461;
U.S. Pat. No. 5,846,437;
U.S. Pat. No. 5,936,359;
U.S. Pat. No. Re36,896;
U.S. Pat. No. 6,126,841;
U.S. Pat. No. 6,149,343;
U.S. Pat. No. 6,217,834; and
U.S. Pat. No. 6,224,759.

Generally, these prior patents relate to ultraviolet radiation fluid treatment systems and/or components for use therein. As is known in the art, ultraviolet radiation is useful to inactivate or kill a wide range of microorganisms (e.g., bacteria., viruses, parasites and the like) which are contained in the fluid being treated.

Thus, the effectiveness of UV radiation for disinfecting high quality effluents has been demonstrated. However, there has been some uncertainty regarding the performance of UV radiation for the disinfection of marginal or poor quality effluents. Underlying this uncertainty is the ability to inactivate particle-associated microorganisms which are highly resistant to UV. High doses of disinfectant are usually required to expose microorganisms buried within particle interiors to lethal doses and in some cases; complete inactivation of particle-associated microorganisms may never be achieved using UV irradiation alone.

Another issue in UV disinfection is the differing sensitivity to UV of the various types of microorganisms (e.g., parasites, bacteria, viruses and the like) which may be present in the fluid. The low UV doses used to inactivate coliforms (an indicator organism which is used to assess the possible level of pathogens) and similarly sensitive pathogens may not inactivate UV-opaque microorganisms to the same level.

Thus, despite the advance made to date there remains room for improvement in the art.

DISCLOSURE OF THE INVENTION

It is an object of the present invention to provide a novel fluid treatment system which obviates or mitigates at least one of the above-mentioned disadvantages of the prior art.

It is another object of the present invention to provide a process for treatment of a fluid which obviates or mitigates at least one of the above-mentioned disadvantages of the prior art.

Accordingly, in one of its aspects, the present invention provides a process for treating a fluid which comprises the step of exposing the fluid to ultraviolet radiation and high-energy ionizing radiation.

In another of its aspects, the present invention provides a fluid treatment system for treatment of a flow of fluid, the system comprising a fluid treatment zone, the fluid treatment zone comprising: a first zone comprising an ultraviolet source and a second zone comprising a high-energy ionizing radiation source.

Thus, the present inventor has surprisingly and unexpectedly discovered that combining ultraviolet radiation with high-energy ionizing radiation in the treatment of a fluid results in synergistic performances of the treatment process—e.g., improvement in the inactivation or killing of microorganisms in the fluid, in destruction of organic contaminants and the like. More specifically, fluid treatment performance is improved to a level typically not possible when using ultraviolet radiation and high-energy ionizing radiation separately.

BRIEF DESCRIPTION OF THE DRAWINGS

Embodiments of the present invention will be described with reference to the accompanying drawings, in which:

FIG. 1 illustrates *E. Coli* inactivation of primary wastewater by ultraviolet irradiation;

FIG. 2 illustrates *E. Coli* inactivation of secondary wastewater by ultraviolet irradiation;

FIG. 3 illustrates *E. Coli* inactivation of primary wastewater by ultraviolet irradiation followed by gamma irradiation; and FIG. 4 illustrates *E. Coli* inactivation of secondary wastewater by ultraviolet irradiation followed by gamma irradiation.

BEST MODE FOR CARRYING OUT THE INVENTION

As used throughout this specification, the term "ionizing radiation" is intended to mean radiation that has sufficient energy to remove bound electrons from the atoms in matter through which the radiation passes. The ionizing radiation spectrum includes ultraviolet radiation, X-radiation, and gamma radiation, in order of increasing energy. As used through out this specification, the term "high-energy ionizing radiation" is intended to mean any form of ionizing radiation (including high-energy particles or electromagnetic waves) that has higher energy than ultraviolet radiation (i.e., ultraviolet radiation is outside the definition of high-energy ionizing radiation).

The present invention relates the synergistic use of UV with other forms of high-energy irradiation, including particle-penetrating irradiation in an integrated disinfection process. The combined use of UV with other forms of irradiation in an integrated disinfection process, which is an aspect of a preferred embodiment of the invention, is an option for addressing a broad range of pathogen sensitivity. The invention could also be used for simultaneous detoxification of organic contaminants, which are typically more sensitive to high-energy ionizing radiation, and inactivation of pathogenic microorganisms, which are typically more sensitive to UV radiation, at low doses.

In a preferred embodiment, the invention relates to a process for liquid treatment, which is beyond the existing radiation treatment technologies. The basic concept of the invention is to combine UV and high-energy ionizing radiation, including high-energy electrons, X-ray radiation and gamma radiation, in an integrated treatment process for fluid treatment to provide complementary and/or synergistic effects.

UV light and high-energy ionizing radiation disinfect aqueous solutions in different ways. The effect of UV is due to a photochemical reaction initiated by the absorption of a photon by a molecular structure. Microorganisms are inactivated by UV light primarily as a result of photochemical damage to nucleic acids. High-energy ionizing radiation has primarily an indirect effect on microorganisms. Irradiation of aqueous material by high-energy ionizing radiation such as high-energy electrons or gamma radiation produces highly reactive unstable intermediates such as hydroxyl radicals, hydrogen atoms, and hydrated electrons. These highly reactive intermediates can cause chemical changes in the aqueous system and within microorganisms, resulting in damage to organisms in the system.

The combination of UV and high-energy ionizing radiation for fluid (e.g., water) treatment provides complementary/synergistic effects. Those microorganisms that are resistant to UV radiation by virtue of being buried within particles can be effectively eliminated by high-energy ionizing radiation. Therefore, disinfection is accomplished more efficiently if UV is carried out at low doses to inactivate free microorganisms and high-energy ionizing radiation processes are used to inactivate particle-associated microorganisms, thereby obviating or mitigating the need for the use of inefficiently high UV or high-energy ionizing radiation doses.

Since the mechanism of microorganism inactivation by UV and high-energy ionizing radiation is different, various genera and species of microorganisms (e.g., parasites, bacteria, viruses, protozoans and the like) have different sensitivity to UV or high-energy ionizing radiation. UV systems or high-energy ionizing radiation systems alone are not well suited, at practical doses, of inactivating highly resistant pathogenic organisms. Combination of UV and other forms of high-energy ionizing radiation provides broad coverage of the electromagnetic radiation spectrum in aqueous solutions. As a result, the inactivation of pathogens is accomplished more efficiently if UV is applied in conjunction with gamma or electron beam radiation.

In its preferred embodiment, the invention allows for substantially complete inactivation of free and particle-associated microorganisms (e.g., bacteria, parasites, protozoans, viruses and the like), adsorbed contaminants and the like through combined use of UV with high-energy ionizing radiation. In its more preferred embodiment, the use of UV, for inactivating free microorganisms, followed by high-energy ionizing radiation, for inactivating particle associated microorganisms, is advantageous since to minimizes the total required energy and consequently energy cost. The invention provides a new method for the treatment of fluid containing particle-associated microorganisms (e.g., bacteria, parasites, protozoans, viruses and the like), adsorbed contaminants and the like, without the requirement for disintegration and/or removal of the particles from the fluid.

The impact of the combination of UV and gamma irradiation on the inactivation of E. coli, an indicator organism, was investigated in primary and secondary wastewater effluents. High-energy electron beam irradiation yields similar water radiolysis products and causes similar water radiation chemistry to that of gamma irradiation. Therefore, it is predictable that results obtained with gamma irradiation in this example would be similar to those that would be obtained with electron beam irradiation.

UV irradiation of the samples showed a linear reduction in $E.$ $coli$ concentration by increasing the radiation dose, at the initial stages of the irradiation. The rate of $E.$ $coli$ inactivation progressively decreased as irradiation proceeded, until it reached a "plateau" or tailing region (FIGS. 1 and 2). The tailing phenomenon is primarily due to the shielding of UV light from microorganisms within particles (Qualls et al., 1983). Microorganisms at particle surfaces are readily disinfected, but interior microorganisms require much longer exposure times (higher apparent dose) to be exposed to the same dose that would inactivate free microorganisms.

Previously UV-irradiated samples were irradiated subsequently by gamma radiation. The primary and secondary wastewater effluent samples were irradiated to various UV doses until reaching the plateau region. The samples were then irradiated to a gamma dose of 250 Gy. The $E.$ $coli$ was completely inactivated after being exposed to gamma irradiation. This indicated that particle associated microorganisms, which are resistant to UV, are being inactivated by high-energy ionizing radiation (FIGS. 3 and 4).

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

BACKGROUND PRIOR ART REFERENCES

Blatchley E. R., Bastian, K. C., Duggirala, R. K., Alleman, J. E., Moore, M., and Schuerch, P., 1996. Ultraviolet Irradiation and Chlorination/Dechlorination for Municipal Wastewater Disinfection, Water Environ. Res., 68, 194

Braunstein, J. L., Loge, F. J., Tchobanoglous, G., and Darby, J. L., 1996. Ultraviolet Disinfection of Filtrated Activated Sludge Effluent for Reuse Applications, Water Environ. Res., 68, 152

Farooq S., Kuruckz C. N., Waite D. W., Cooper W.; 1993. "Disinfection of waste waters: High Energy Electron vs Gamma Irradiation"; Wat. Res., 27, 7, 1177-1184

Gualls, R. G., Flynn, M. P., and Johnson, J. D. 1983. The Role of Suspended Particles in Ultraviolet Disinfection. J. Water Pollut. Control Fed. 55, 1280-1285

International Atomic Energy Agency, 1997. Technical Document, GC(41)/INF/5

International Atomic Energy Agency, 1990. Technical Document, Proc., Joint ASCE-IAEA Meeting on Radiation Treatment, Washington D.C., July 1990

Oppenheimer A. J., Jacangelo J. G., Lane J. M., Hoagland J. E, 1997. Testing the Equivalency of Ultraviolet light and Chlorine for Disinfection of Wastewater to Reclamation Standards, Water Environ. Res., 69, 14-24

Pribil W., Sommer R., Appelt S., Gehringer P., Eschweiler H., Cabaj H. L. A., Haider T., 2000. Inactivation of Indicator Bacteria and Indicator Viruses by Ionizing Radiation, University of Vienna Rawat K. P., Sharma A., and Rao S. M., 1998. "Microbiological and Physical Analysis of Radiation Disinfected Municipal Sewage" Wat. Res. 32,3,pp737-740

Sakamoto, G., 1997. UV Disinfection For Wastewater Reclamation, Proc.1997 PNPCA Annual Conference "Clean Water for the 21st Century, Doing More for Less", Seattle, Wash., October, 1997

Scheible O. K., Casey, M. C., and Forndran, A., 1986. Ultraviolet Disinfection of Wastewater from Secondary Effluent and Combined Sewer Overflows. EPA/600/2-86/005, PB86-145182, 1986, U.S. Environmental Protection Agency, Cincinnati, Ohio Thompson, J. A., and Blatchley, E. R., 1998. Anti-Microbial Effects of Gamma Irradiation for Disinfection of Water and Wastewater, Proc. Disinfection 98: The latest Trends in WasteWater Disinfection, Water Environment Federation, April 1998, Baltimore, Md.

Thompson, J. A., and Blatchley, E. R. 2000. Gamma irradiation for inactivation of *C. parvum, E. coli*, and Coliphage MS-2, Journal of Environmental Engineering, August 2000

U.S.EPA 1992. Ultraviolet Disinfection Technology Assessment. EPA 832-R-92-004, PB92-222868, U.S. Environmental Protection Agency, Washington, D.C.

Whitby, G. E. and Palamer, G., 1993. The effect of UV Transmission, Suspended Solids and Photoreactivation on Microorganisms in Wastewater Treated with UV Light, Wat. Sci. Tech., 27, 379

Zukovs, G., Kollar, J., Monteith, H. D., Ho, K. W. A., and Ross, S. A., 1986. Disinfection of Low Quality Wastewaters by Ultraviolet Light Irradiation, J. Water Pollut. Control Fed., 58, 199

What is claimed is:

1. A process for treating water comprising a plurality of microorganisms which comprises the steps of:
   (i) exposing the water to ultraviolet radiation having a first dose to cause photochemical damage to nucleic acids in a first portion of the plurality of the microorganisms; and
   (ii) exposing the water to high-energy ionizing radiation to cause the production of intermediates that are reactive with a second portion of the plurality of the microorganisms, wherein the second portion is not photochemically damaged by the ultraviolet radiation, and the first dose is less than a dose sufficient to cause photochemical damage in both the first and second portions of the plurality of the microorganisms.

2. The process defined in claim 1, wherein exposure to ultraviolet radiation and high-energy ionizing radiation is conducted sequentially.

3. The process defined in claim 1, wherein exposure to ultraviolet radiation and high-energy ionizing radiation is conducted concurrently.

4. The process defined in claim 1, wherein the water is first exposed to ultraviolet radiation and then to high-energy ionizing radiation.

5. The process defined in claim 1, wherein the water is first exposed to high-energy radiation and then to ultraviolet radiation.

6. The process defined in claim 1, wherein the water is gravity fed through a treatment zone comprising a first zone comprising an ultraviolet source and a second zone comprising a high-energy ionizing radiation source.

7. The process defined in claim 6, wherein the treatment zone comprises an open channel comprising a flow of the water.

8. The process defined in claim 6, wherein the treatment zone comprises a closed chamber which confines the water within a predefined maximum distance from at least one of the ultraviolet source and the high-energy ionizing radiation source.

9. The process defined in claim 6, wherein the treatment zone comprises a closed chamber which confines the water within a predefined maximum distance from both of the ultraviolet source and the high-energy ionizing radiation source.

10. The process defined in claim 6, wherein at least one of the ultraviolet radiation source and the high-energy ionizing radiation source is submersible in the water being treated.

11. The process defined in claim 6, wherein the ultraviolet radiation source is elongate and is disposed substantially parallel to the direction of the flow of water.

12. The process defined in claim 6, wherein the ultraviolet radiation source is elongate and is disposed substantially transverse to the direction of the flow of water.

13. The process defined in claim 6, wherein the high-energy ionizing radiation source comprises a point source, a spherical source, an annular source or a flat source.

14. The process defined in claim 6, wherein the high-energy ionizing radiation source is remote from the flow of water.

15. The process defined in claim 6, wherein the ultraviolet radiation source comprises a low pressure ultraviolet radiation source.

16. The process defined in claim 6, wherein the ultraviolet radiation source comprise a medium pressure ultraviolet radiation source.

17. The process defined in claim 1, wherein the high-energy ionizing radiation comprises high-energy electrons.

18. The process defined in claim 1, wherein the high-energy ionizing radiation comprises gamma radiation.

19. The process defined in claim 1, wherein the high-energy ionizing radiation comprises X-ray radiation.

20. The process defined in claim 1, wherein the water is a secondary effluent.

21. A process for treating a fluid containing microorganisms, which process comprises the step of exposing the fluid to ultraviolet radiation having a first dose and high-energy ionizing radiation selected from one or both of high energy electrons and gamma radiation, wherein the first dose is less than a dose sufficient to cause photochemical damage to nucleic acids in all microorganisms in the fluid.

22. The process defined in claim 21, wherein exposure to ultraviolet radiation and high-energy ionizing radiation is conducted sequentially.

23. The process defined in claim 21, wherein exposure to ultraviolet radiation and high-energy ionizing radiation is conducted concurrently.

24. The process defined in claim 21, wherein the water is first exposed to ultraviolet radiation and then to high-energy ionizing radiation.

25. The process defined in claim 21, wherein the water is first exposed to high-energy radiation and then to ultraviolet radiation.

26. The process defined in claim 21, wherein the water is gravity fed through a treatment zone comprising a first zone comprising an ultraviolet source and a second zone comprising a high-energy ionizing radiation source.

27. The process defined in claim 21, wherein the high-energy ionizing radiation consists of high-energy electrons.

28. The process defined in claim 21, wherein the high-energy ionizing radiation consists of gamma radiation.

29. A process for treating water comprising free microorganisms and particle-associated microorganisms, the process comprising the steps of:
  (i) exposing the water to ultraviolet radiation having a first dose to cause photochemical damage to nucleic acids in the free microorganisms; and
  (ii) exposing the water to high-energy ionizing radiation to cause the production of intermediates that are reactive with the particle-associated microorganisms, wherein the particle-associated microorganisms is not photochemically damaged by the ultraviolet radiation, and the first dose is less than a dose sufficient to cause photochemical damage in both the free microorganisms and the particle-associated microorganisms.

30. The process defined in claim 29, wherein the water is a primary effluent.

31. The process defined in claim 29, wherein the water is a secondary effluent.

32. The process defined in claim 1, wherein the water is a primary effluent.

* * * * *